(12) United States Patent
Waxler

(10) Patent No.: US 9,301,738 B2
(45) Date of Patent: Apr. 5, 2016

(54) TISSUE SAMPLE SECUREMENT AND EXTRACTION APPARATUS AND METHOD

(71) Applicant: Donald R. Waxler, Barrington, IL (US)

(72) Inventor: Donald R. Waxler, Barrington, IL (US)

( * ) Notice: Subject to any disclaimer, the term of this patent is extended or adjusted under 35 U.S.C. 154(b) by 92 days.

(21) Appl. No.: 14/276,133

(22) Filed: May 13, 2014

(65) Prior Publication Data

US 2014/0343453 A1 Nov. 20, 2014

Related U.S. Application Data

(60) Provisional application No. 61/823,052, filed on May 14, 2013.

(51) Int. Cl.
*A61B 10/00* (2006.01)
*A61B 10/02* (2006.01)

(52) U.S. Cl.
CPC ......... *A61B 10/0275* (2013.01); *A61B 10/0266* (2013.01); *A61B 2010/0208* (2013.01)

(58) Field of Classification Search
CPC ... A61B 17/221; A61B 10/04; A61B 10/0275
USPC .................................. 600/562, 570; 606/113
See application file for complete search history.

(56) References Cited

U.S. PATENT DOCUMENTS

| | | | |
|---|---|---|---|
| 2,137,710 A | 11/1938 | Anderson | |
| 2,670,519 A | 3/1954 | Recklitis | |
| 3,989,049 A | 11/1976 | Yoon | |
| 4,103,680 A | 8/1978 | Yoon | |
| 4,174,715 A | 11/1979 | Hasson | |
| 4,427,014 A | 1/1984 | Bel et al. | |
| 5,569,299 A | 10/1996 | Dill et al. | |
| 5,759,187 A | 6/1998 | Nakeo et al. | |
| 6,273,860 B1 | 8/2001 | Kostylev et al. | |
| 6,569,105 B1 | 5/2003 | Kortenbach et al. | |
| 8,226,575 B2 | 7/2012 | Levy | |
| 8,360,950 B2 | 1/2013 | Acosta et al. | |
| 2004/0181169 A1 | 9/2004 | Diamond et al. | |
| 2006/0178699 A1 | 8/2006 | Surti | |
| 2006/0195118 A1* | 8/2006 | Richardson | A61B 17/221 606/113 |
| 2006/0258955 A1 | 11/2006 | Hoffman et al. | |
| 2007/0055172 A1 | 3/2007 | Ratnakar | |
| 2007/0060839 A1* | 3/2007 | Richardson | A61B 10/04 600/570 |
| 2007/0073185 A1 | 3/2007 | Nakao | |
| 2009/0227892 A1 | 9/2009 | Krombach et al. | |
| 2010/0228221 A1 | 9/2010 | Kassab | |

* cited by examiner

*Primary Examiner* — Brian Szmal
(74) *Attorney, Agent, or Firm* — Meroni & Meroni, PC; Charles F. Meroni, Jr.

(57) ABSTRACT

A tissue sample securement apparatus secures a volumetric tissue sample. The tissue sample securement apparatus according to the present invention includes an expandable-retractable tissue sampling device, which tissue sampling device includes an axial displacement member, an expandable tip construction, and a tensile member. The axial displacement member includes a distal member end and a proximal member end. The tip construction extends from the distal member end, and the tensile member extends in adjacency to the axial displacement member and is connected to the tip construction for selectively retracting a member-retractable distal portion of the tip construction. The selectively retracted distal portion simultaneously severs and secures a volumetric tissue sample. The tissue sample may then be retrieved via a catheter member for directing the device to and from the target tissue mass.

12 Claims, 6 Drawing Sheets

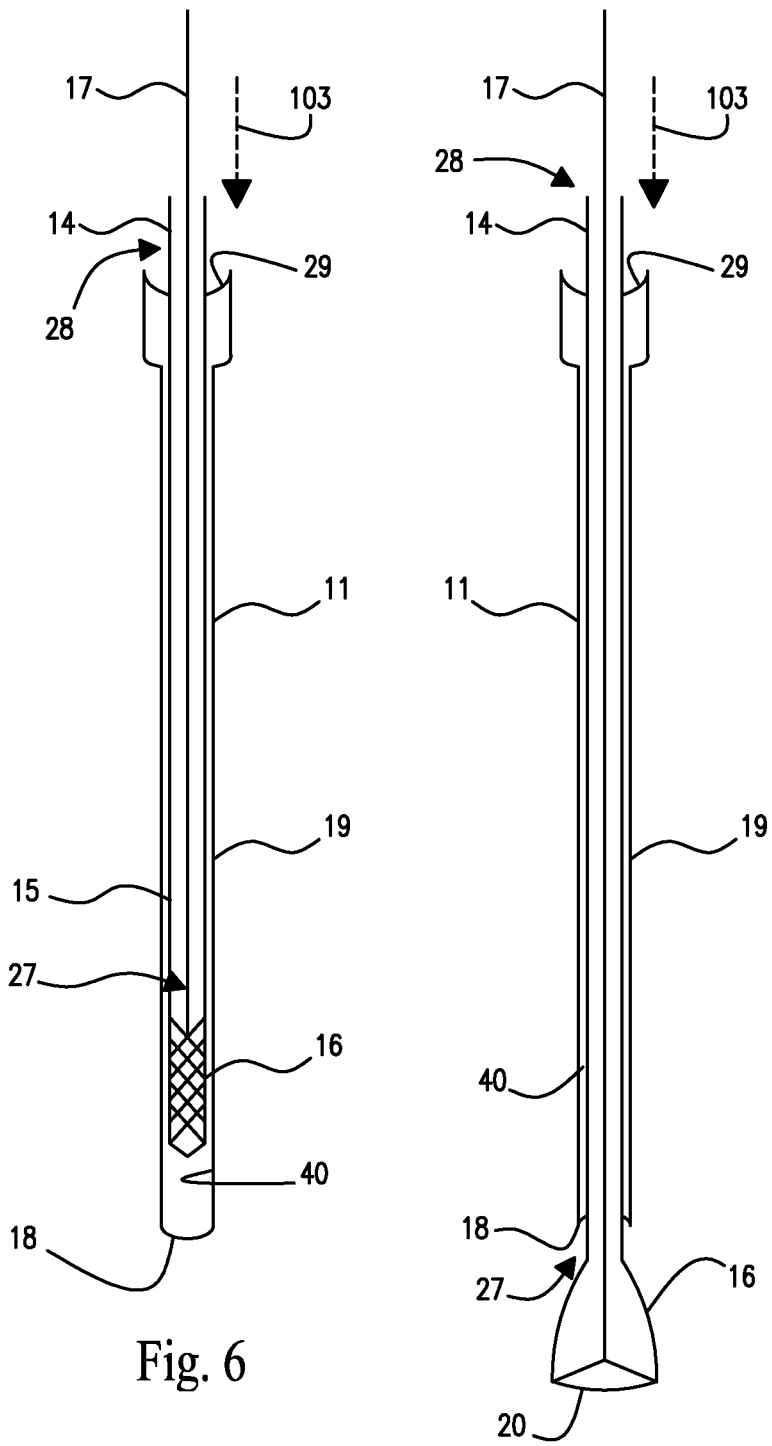

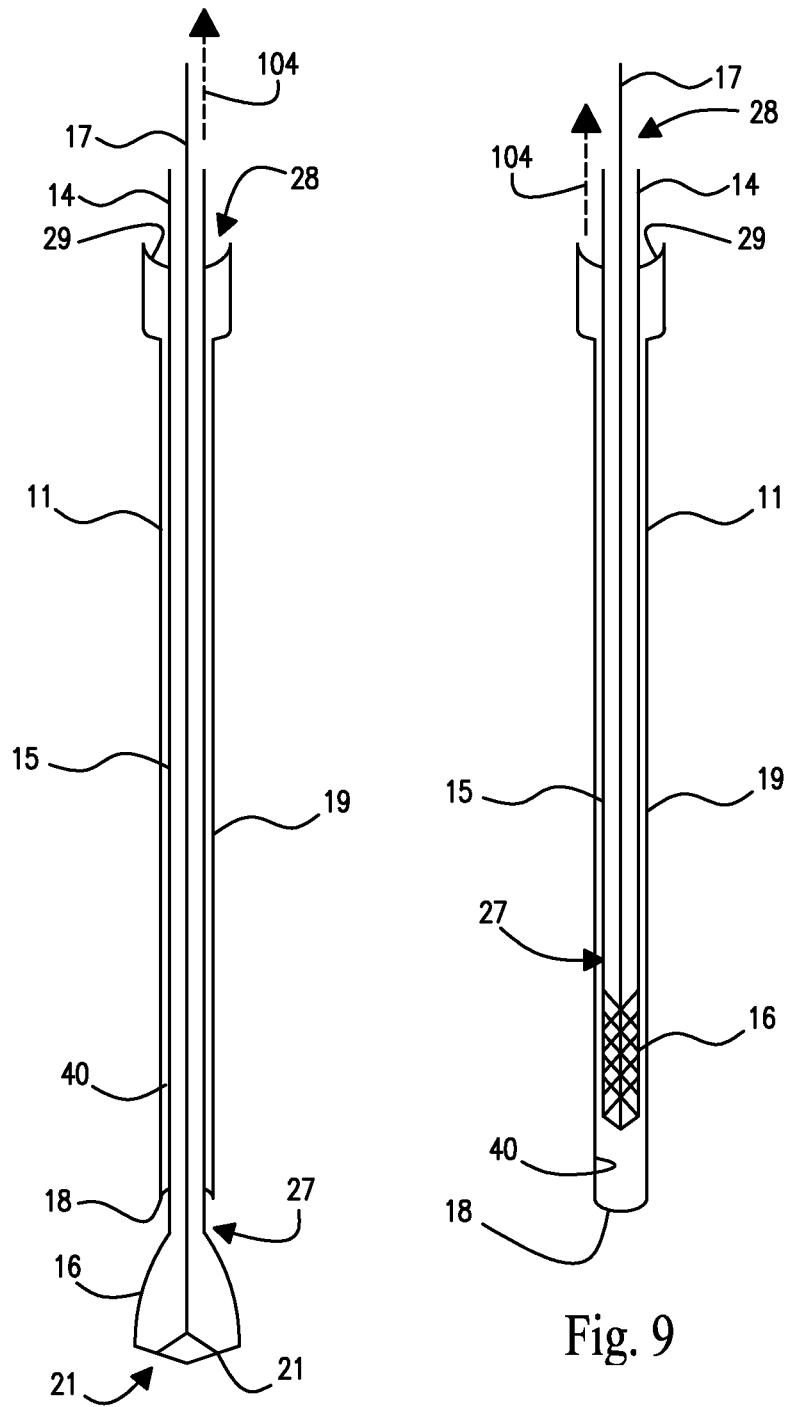

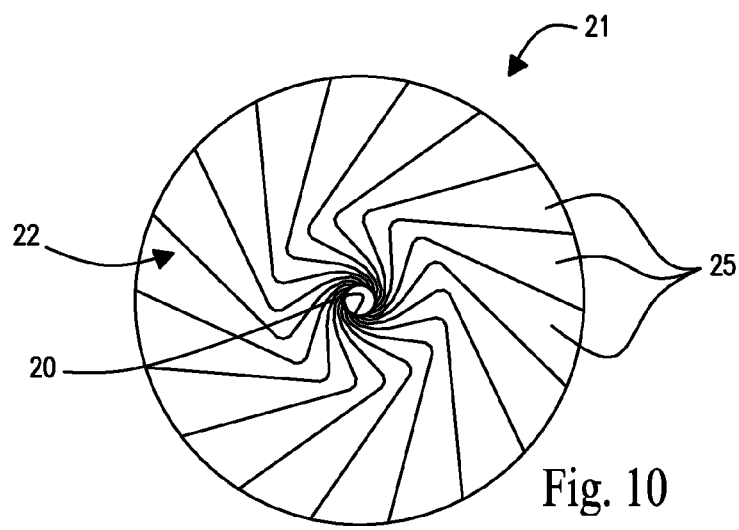
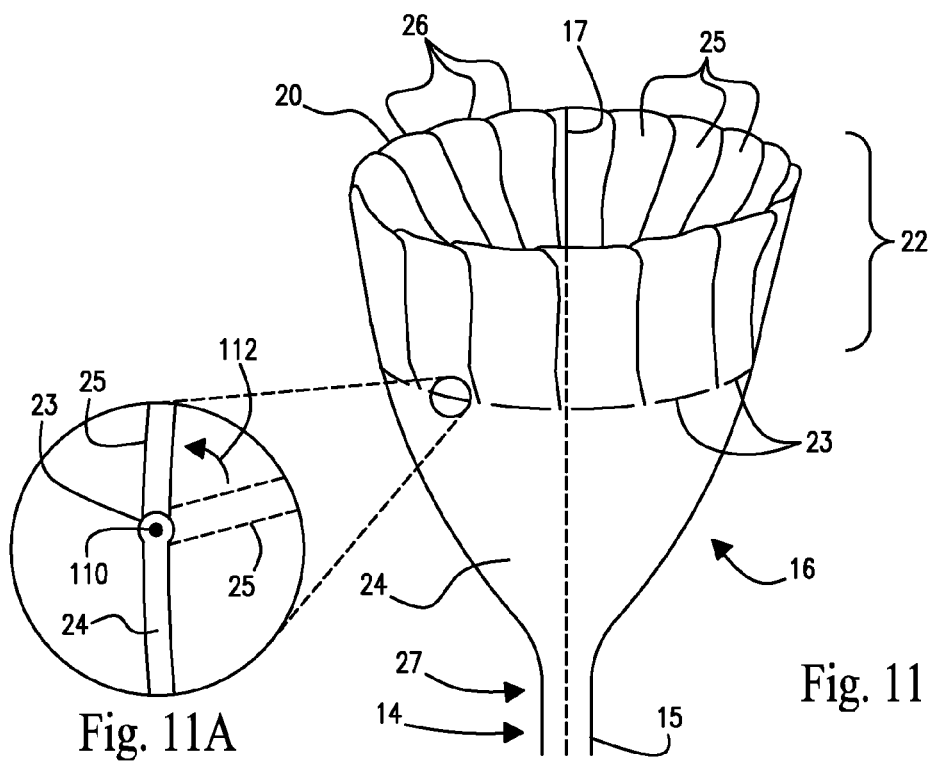

TISSUE SAMPLE SECUREMENT AND EXTRACTION APPARATUS AND METHOD

PRIOR HISTORY

This non-provisional patent application claims the benefit of U.S. Provisional Patent Application No. 61/823,052, filed in the United States Patent and Trademark Office on 14 May 2013.

BACKGROUND OF THE INVENTION

1. Field of the Invention

The present invention generally relates to a tissue sampling mechanism for use as a diagnostic tool. More particularly, the present invention relates to a tissue sampling mechanism primarily designed for use in biopsy procedures, which tissue sampling mechanism is designed to collect relatively larger tissue samples as compared to state of the art tissue collection devices.

2. Discussion of the Prior Art

Many physicians in many specialties need to determine if tissues seen on imaging studies are normal or abnormal. Abnormal tissue can be cancerous and therefor later require surgical removal, chemotherapy or radiation therapy. One common or traditional method for determining whether tissue is abnormal is to do a needle biopsy. A needle biopsy is advantageous because it has few complications and does not require surgery or anesthesia. For example, if an abnormal area or abnormal calcification is seen on a mammogram, a needle biopsy of the abnormality is commonly performed. The tissue sample obtained from the needle biopsy can then be analyzed to determine and/or confirm whether the tissue is abnormal.

Some of the prior art relating to biopsy needles and other similar surgical or medical tools for securing samples of tissue or matter and the like are briefly described hereinafter. U.S. Pat. No. 2,137,710 ('710 patent), which issued to Anderson, for example, discloses certain Forceps. The '710 patent describes certain forceps comprising a tubular body, a single length of wire bent midway between its ends and located in said tubular body. The wire forms fingers which cross each other near their free ends and near the bent portion of said wire within said tubular body.

The forceps further comprise actuating means connected to the bent portion of said wire and movable relatively to the tubular body for extending said fingers beyond the mouth of the tubular body in divergent, quickly spreading arcuate directions. From a comparative inspection of FIGS. 1 and 2 of the '710 patent, it will be seen that tissue sampling ends 19 and 20 of fingers 14 and 15 selectively protrude from and retract into the tube 10 for grabbing tissues and the like.

U.S. Pat. No. 2,670,519 ('519 patent), which issued to Recklitis, discloses a Drainage Tube with Clot Extractor. The '519 patent essentially describes an embalming implement comprising an outer tube formed with a lateral opening in one end portion, an inner tube slidably and rotatably fitted within the outer tube and formed with a lateral opening alignable with the lateral opening in the outer tube, the end of the inner tube adjacent its lateral opening being closed and it other end being open, and a plurality of resilient prongs on the other end of the inner tube constructed and arranged to be received within the outer tube and to project in expanded relation beyond the outer tube when said lateral openings are aligned. From a comparative inspection of FIGS. 1 and 3 of the '519 patent, it will be seen that clot-grabbing ends 38 selectively protrude from and retract into the tube 10 for grabbing clots and the like.

U.S. Pat. No. 4,174,715 ('715 patent), which issued to Hasson, discloses certain Multi-Pronged Laparoscopy Forceps. The '715 patent describes multi-pronged spring-loaded laparoscopy instruments are provided for use in tubal sterilization, ovarian mobilization and biopsy. The instruments include three or four expandable prongs for holding tissue in a stable position. The instrument may be provided with a plug for access to an inner biopsy channel or central bore for facilitating ovarian biopsy.

A slotted bushing may be provided with offset apertures to enable the surgeon to hold the prongs in preselected positions without exerting pressure on the handle of the instrument. When desired, the instrument may be provided with a manually remote-controlled cutting edge at the forward tip of the instrument to re-sect a segment of the coagulated tube during tubal sterilization.

Referencing Column No. 5, Line Nos. 25-36, you will please note that the '715 patent further describes that the four-pronged laparoscopy forceps may also be used as a surgical cutting blade. The forwardmost circular edge of outer tube 29 being razor sharpened may be extended or retracted along tubular sleeve 26 by rotating collar 45. As the collar rotates, the stud 47 follows the spiral groove in guide sleeve 25 to translate the collar and the outer tube on the tubular sleeve. When the collar is rotated to its forwardmost position, the sharpened circular edge extends beyond the prongs. The diameter of tube 29, however, does not expand.

U.S. Pat. No. 4,427,014 ('014 patent), which issued to Bel et al., discloses Biopsy Forceps. The '014 patent describes biopsy forceps for use with a contact endoscope having a body terminating in a distal end comprising a hollow outer tube open at both ends, a hollow inner tube located coaxially within the outer tube, the inner tube being open at its rear end and terminating at its front end in at least one pair of diametrically opposed tongues that extend outwardly beyond the front end of the outer tube and in a direction substantially parallel to the longitudinal axis of the tubes and then bend inwardly at their far end at right angles to the longitudinal axis terminating in a series of teeth to form forceps jaws.

The jaws are biased in a direction away from the axis, whereby movement of the tubes in one direction relative to one another causes the tongues of the jaws to slide into the outer tube and the forceps jaws to close and movement in the opposite direction causes the jaws to open, and a control device for axially moving one of the tubes relative to the other to activate the jaws, whereby the endo scope can be inserted all the way through the forceps from its rear end so that the distal end of the endoscope lies against the forceps jaws.

U.S. Pat. No. 5,759,187 ('187 patent), which issued to Nakao et al., discloses certain Surgical Retrieval Assembly and Associated Method. The '187 patent describes a method for removing a polyp from a patient utilizes (i) a flexible conductive cauterization loop and (ii) a flexible auxiliary loop to which a flexible web member is connected to define an expandable pocket, the cauterization loop and the auxiliary loop being disposed in a common tubular member. Upon insertion of an endoscope assembly into a patient and a locating of the polyp, the tubular member is moved through the biopsy channel of the endoscope to eject a distal end portion of the tubular member from the biopsy channel.

The cauterization loop is then shifted in a distal direction relative to the ejected tubular member to eject the cauterization loop from the tubular member. The cauterization loop is manipulated from outside of the patient to pass the loop over the polyp and to at least partially close the loop to engage the polyp around a base region thereof.

Upon a subsequent conducting of an electrical current through the cauterization loop to burn through the polyp at the base region, thereby severing the polyp at the base region, the cauterization loop is retracted into the tubular member and the auxiliary loop is ejected and maneuvered to enclose the severed polyp in the capture pocket. The auxiliary loop is at least partially closed to capture the severed internal body tissues in the pocket. The captured polyp is removed in the pocket from the patient.

U.S. Pat. No. 6,273,860 ('860 patent), which issued to Kostylev et al., discloses a Biopsy Apparatus. The '860 patent describes an endoscopic instrument having one or two moving jaws. One or two control wires attach to the lower portion of the moving jaws. Each control wire is located within a groove or enclosed channel which passes along the side and preferably to the back of the jaw.

The end of the control wire is connected with the jaw so that when the control wire is moved, the force from the wire moved the jaw about its pivot point. If two moving jaws are present, the pivot point is preferably centrally located in the housing. If only a single moving jaw is used, the pivot point may be central, or it may be offset. The control wire is arguably similar to a pull cord insofar as it operates to direct a pulling force to the mechanism it operates.

In this last regard, U.S. Pat. No. 6,569,105 ('105 patent) is also pertinent. The '105 patent, which issued to Kortenbach et al, discloses Method Rotatable and Deflectable Biopsy Forceps. The '105 patent describes an endoscopic or laparoscopic biopsy forceps instrument is provided which includes a flexible tubular member having proximal and distal ends, a biopsy jaw assembly at the distal end of the tubular member, an actuation assembly to operate the jaw assembly between open and closed positions, and a control assembly to deflect the biopsy jaw assembly relative to a lumen through which the instrument extends and to rotate the jaw assembly about the longitudinal axis of the instrument.

U.S. Pat. No. 8,226,575 ('575 patent), which issued to Levy, discloses Biopsy Needle Assemblies. The '575 patent provides needle biopsy systems and methods for obtaining tissue biopsies. In various embodiments, the systems and methods provided can inhibit needle contamination by unwanted tissue or cells and/or regulate a negative pressure to assist sampling of target tissue or cells. The reader may wish to reference FIG. 34, which figures depict a biopsy needle having a tissue sampling mechanism in a deployed position relative to the needle body.

United States Patent Application No. 2006/0178699, which was authored by Surd, describes biopsy forceps and method(s) of using the biopsy forceps. The biopsy forceps includes a plurality of grasping members extending from an inner shaft. The plurality of grasping members is biased toward an open configuration. Sliding a sheath over the grasping members constrains the grasping members to a closed configuration. The reader will note that the ends of the grasping members may be outfitted with blades as referenced at 33.

United States Patent Application No 2009/0227892, which was authored by Krombach et al., describes a catheter device for percutaneous interventions, in particular for injections, biopsies or the like, with an outer catheter and with a tool for the intervention, in particular an injection needle, biopsy forceps, electrodes or the like, at the proximal end of the catheter device.

To be able to perform a percutaneous intervention free of injury, the tool is received in the outer catheter in the delivery state, and the tip of the tool is recessed in the outer catheter in the delivery state or aligned with the proximal end of the outer catheter, and the tool can be moved relative to the outer catheter in such a way that at least the tip of the tool protrudes past the proximal end of the outer catheter in the state of engagement.

United States Patent Application No. 2010/0228221, authored by Kassab, describes devices, systems, and methods for accessing tissue in a minimally invasive manner and taking a biopsy tissue sample. At least some of the embodiments disclosed herein enable a tissue sample to be taken from the external surface of the heart in a non-invasive manner. In addition, various disclosed embodiments provide devices, systems and methods for accessing the pericardial space through the interior of the heart and engaging the epicardial surface and removing a tissue sample therefrom for diagnostic purposes through the use of suction. The reader may wish to reference FIGS. 16(a)-18(b) which references a collapsible skirt, which skirt does not appear to provide any cutting function.

From a consideration of the foregoing art particularly and the field of art generally, it will be seen that the prior art perceives a need for a tissue sampling mechanism that provides an expandable skirt-like structure, which when expanded defines a volumetric tissue sample-securing space and a planar circular cutting terminus for cutting into the tissue sample to be or secured. Further, the prior art perceives a need for such a device wherein the circular cutting terminus is cinchable for further cutting and enclosing the tissue sample to be secured within the skirt-like structure. Accordingly, the present invention provides such a mechanism, as summarized in more detail hereinafter.

SUMMARY OF THE INVENTION

The author, in 2013, observed an infusion procedure by a then state of art expandable catheter. The typical state of the art expandable catheter, as it axially displaces and extends out of an outer sheath catheter, widens or expands to enlarge to the diameter of the artery in which it is located. This observation sparked the author's conception that instead of using an expandable tip of such a catheter for infusion purposes, such a tip could be made expandable for biopsy purposes.

The advantage of this expandable biopsy catheter is that it will operate to retrieve larger volumes of biopsy sample tissue. As the catheter is expandable, pliable, or volume-definable, it can be structurally configured so as to acquire a larger amount of cells than a standard or state of the art biopsy catheter, which state of the art biopsy catheter typically has a diameter on the same order as that of the outer sheath.

Accordingly, a primary advantage of the present invention is that the device enables the tissue sampler to secure a single relatively high volume tissue sample. The relatively high volume tissue sample obtained from a single pass is only achievable by way of state of the art biopsy needles or catheters via multiple or many biopsy passes.

In other words, current biopsy devices are typically the same size as the introducing needle. The current devices are advanced though an introducer needle into the abnormal tissue. The biopsy needle sample retrieved is then retracted into the introducer needle, removed from the needle, and then the sample is placed into a container to be sent to pathology evaluation. The sample volume secured is typically defined by the sample-securing opening and the diameter of the introducer needle.

This feature requires the state of the art biopsy device to be passed many times in order to sample multiple areas of the abnormal tissue in order to obtain a sufficient amount of tissue. By contrast, the present invention provides an expandable biopsy device that is able to retrieve a relatively more voluminous amount of sample tissue in a single pass when extended out of the introducing needle. This avoids the problem of multiple passes to secure an adequate sample volume other required by current biopsy devices.

A primary objective of the present invention is thus to provide a device or mechanism or method for obtaining an adequate tissue sample volume in fewer passes. To achieve this primary objective, the present invention essentially employs an outer catheter with a sharpened tip and internal stylet that are advanced in abnormal tissue mass requiring biopsy. This is typically performed with fluoroscopic, ultrasound, or CT localization guidance.

The inner stylet of the catheter is then removed. The inner stylet is replaced by an expandable and retractable flexible tip biopsy catheter. As the expandable biopsy catheter is advanced and axially displaced relative to the outer catheter, the tip emerges from the end of the outer catheter, and flares outward or expands in the appearance of an inverted umbrella.

The outer tip or distal end of the expandable biopsy catheter is manufactured to comprise a razor sharp cutting edge. As this razor sharp cutting edge is advanced into the target tissue mass, it cuts the tissue and the cut tissue advances into the volumetric spaced defined by the expanded umbrella-like tip. The razor sharp cutting edge is on a hinge at the end of the expandable biopsy catheter.

A pull wire is embedded in the wall of the expandable biopsy catheter with the end of the wire attached or anchored to the razor sharp cutting end. By applying tension to the wire the anchor point will force the razor sharp cutting end in a direction that operates to cinch the end and enclose the volumetric space thereby securing the tissue sample volume.

In other words, when an adequate biopsy sample volume is obtained within the volumetric space defined by the inside of the expandable tip, the outer razor edge is pulled and bent inward by the pull wire that is embedded in the wall of the biopsy catheter. Pulling of the wire draw mechanism causes the razor edge to be flexed inward and cuts off the end of the biopsy sample. This wire draw mechanism closes the end of the expandable tip catheter.

The expandable tip catheter is then retracted as it is axially displaced back into the outer catheter with the biopsy sample enclosed within the retracted expandable tip. The expandable catheter is then removed from the outer catheter. When the expandable catheter is outside of the patient, the wire is then relaxed and the tip of the catheter re-expands. The volumetric biopsy tissue sample is then released and placed in a sterile container to be sent to the pathology department for pathology evaluation.

BRIEF DESCRIPTION OF THE DRAWINGS

Other features of my invention will become more evident from a consideration of the following brief descriptions of preliminary drawings of the subject invention(s):

FIG. 6 is a diagrammatic perspective type depiction of the expandable-retractable biopsy sampling device according to the present invention shown received inside a fragmentary prior art outer catheter, the outer catheter having parts broken away to show the sampling device having a tubular portion and a lower expandable basket-like tip depicted in a retracted state and being directed in a first direction from a first axial position relative to the outer catheter.

FIG. 7 is a diagrammatic perspective type depiction of the expandable-retractable biopsy sampling device according to the present invention shown received inside a fragmentary prior art outer catheter, the outer catheter having parts broken away to show the sampling device having a tubular portion and a lower expandable basket-like tip depicted in an expanded state and being directed in a first direction from a second axial position relative to the outer catheter.

FIG. 8 is a diagrammatic perspective type depiction of the expandable-retractable biopsy sampling device according to the present invention shown received inside a fragmentary prior art outer catheter, the outer catheter having parts broken away to show the sampling device having a tubular portion and a lower expandable basket-like tip depicted in a retracted state and being directed in a second direction to the second axial position relative to the outer catheter.

FIG. 9 is a diagrammatic perspective type depiction of the expandable-retractable biopsy sampling device according to the present invention shown received inside a fragmentary prior art outer catheter, the outer catheter having parts broken away to show the sampling device having a tubular portion and a lower expandable basket-like tip depicted in an expanded state and being directed in the second direction to the first axial position relative to the outer catheter.

FIG. 10 is an axial view of the expandable basket-like tip shown in a cinched, tissue sample-enclosed/secured state.

FIG. 11 is a top perspective view of the expandable basket-like tip shown in an expanded, tissue-cutting structural configuration or state.

FIG. 11A is an enlarged, fragmentary cross-sectional view of a hinge junction between a proximal portion of the basket-like tip construction and a distal cutting blade of the basket-like tip construction according to the present invention.

DETAILED DESCRIPTION OF THE PREFERRED EMBODIMENT AND METHOD

Figure 1:
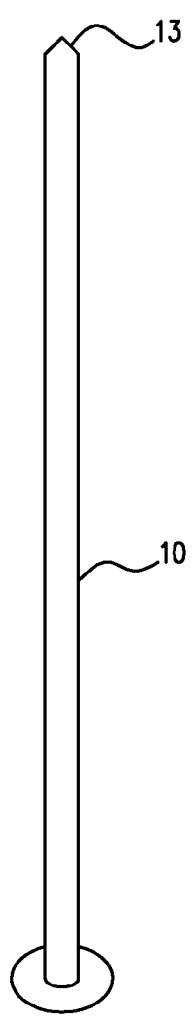
FIG. 1 is a perspective view of a prior art pointed inner stylet of an initial introducer assembly.
Figure 2:
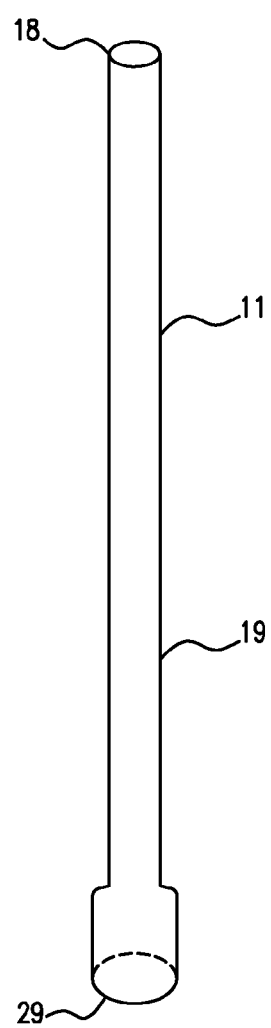
FIG. 2 is a perspective view of a prior art outer catheter of an initial introducer assembly.
Figure 3:
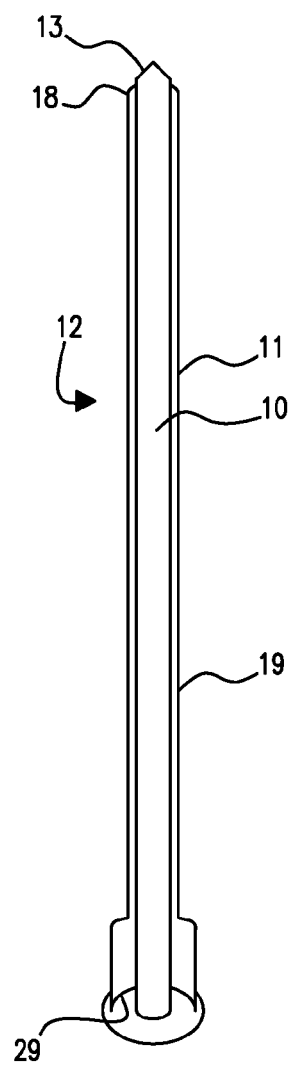
FIG. 3 is a perspective view of a prior art initial introducer assembly comprising an inner pointed stylet and an outer catheter with portions of the outer catheter broken away to show the inner pointed stylet.

Referring to the drawings now with more specificity, the reader is first directed to FIGS. 1-3. From a comparative inspection of FIGS. 1-3, it will be seen that a prior art stylet 10 (as depicted in FIG. 1) and prior art catheter construction (as depicted in FIG. 2) are cooperable. The prior art stylet 10 is insertable or telescopically receivable in the prior art outer catheter 11 as generally depicted in FIG. 3.

Figure 12:
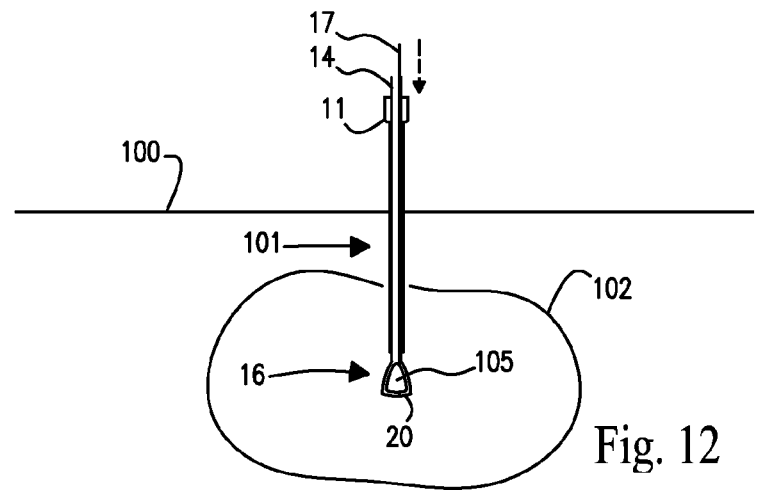
FIG. 12 is a diagrammatic depiction of the expandable-retractable biopsy sampling device according to the present invention being directed in a first direction relative to the outer catheter, expanded, and cut-inserted into a sub-dermal tissue mass for cutting into a volumetric portion of the tissue mass for securing a volumetric biopsy tissue sample.
Figure 13:
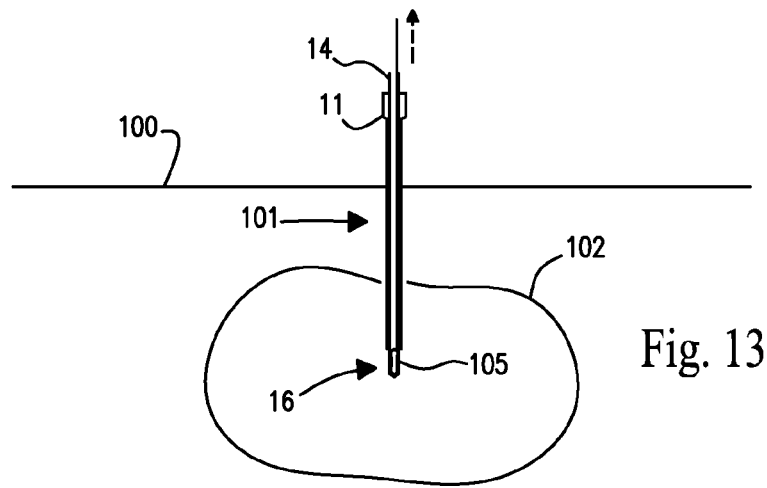
FIG. 13 is a diagrammatic depiction of the expandable-retractable biopsy sampling device according to the present invention being directed in a second direction relative to the outer catheter, retracted, and cinched at the terminal end for enclosing-capturing the volumetric portion of the tissue mass for securing the volumetric biopsy tissue sample.
Figure 14:
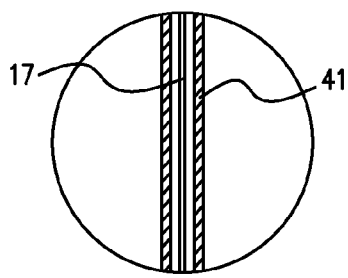
FIG. 14 is a longitudinal cross-sectional view of an inner-tubular, wall-embedded draw wire according to the present invention, which draw wire functions to cinch close the terminal end of the expandable basket-like tip.
Figure 15:
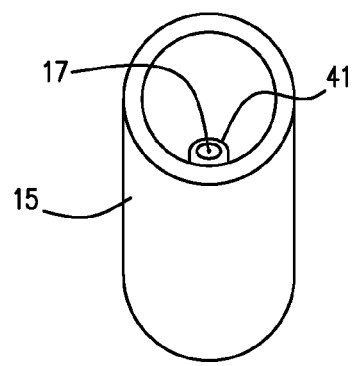
FIG. 15 is a fragmentary perspective view of the inner-tubular, wall-embedded draw wire according to the present invention, which draw wire functions to cinch close the terminal end of the expandable basket-like tip.

This ensemble 12 and the methods enabled thereby essentially function to pierce the superficial dermal layer 100 and sub-dermal tissue layers 101 via the pointed end 13 of the stylet 10 to localize the outer catheter 11 adjacent the targeted tissue mass 102 as an instrument delivery guide or conduit to the targeted tissue mass 102 for tissue sampling as generally and comparatively depicted in FIGS. 12 and 13.

Once the outer catheter 11 is in positioned placement adjacent the targeted tissue mass 102, the inner stylet 10 can be removed from the ensemble 12 by directing the inner pointed stylet 10 in a first direction, thereby axially displacing the same relative to the stationary outer catheter 11 disassembling the ensemble 12, and enabling receipt of a subsequent instrument (e.g. the expandable-retractable biopsy sampling device 14 according to the present invention) therein.

Figure 4:
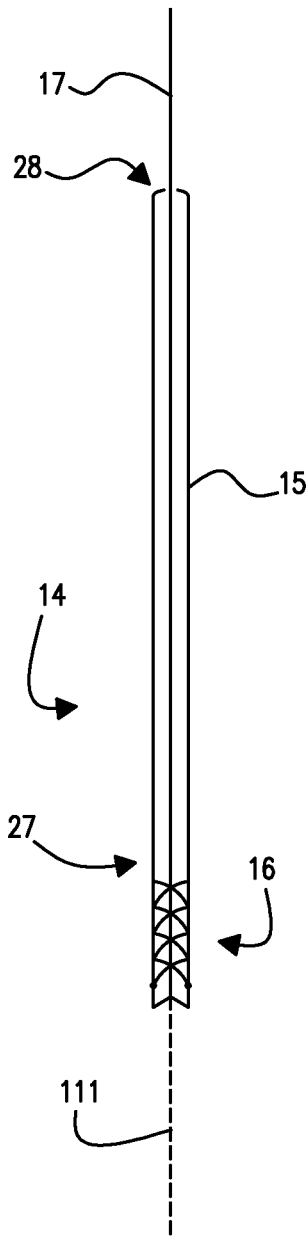
FIG. 4 is a diagrammatic depiction of an expandable/retractable biopsy sampling device according to the present invention showing a tubular portion, a lower expandable basket-like tip depicted in a retracted state, and a draw wire extending from the tip through the length of the tubular portion.

FIG. 4 generally shows a diagrammatic depiction of the expandable/retractable biopsy sampling device 14 according to the present invention showing a tubular portion or axially displacement member as at 15; a lower expandable basket-like tip construction as at 16, which tip construction 16 is depicted in a retracted state in FIG. 4; and certain tip retraction means as exemplified by a draw wire or tensile member 17 extending from the tip construction 16 through the length or in adjacency to the length of the tubular portion or axial displacement member 15.

Figure 5:
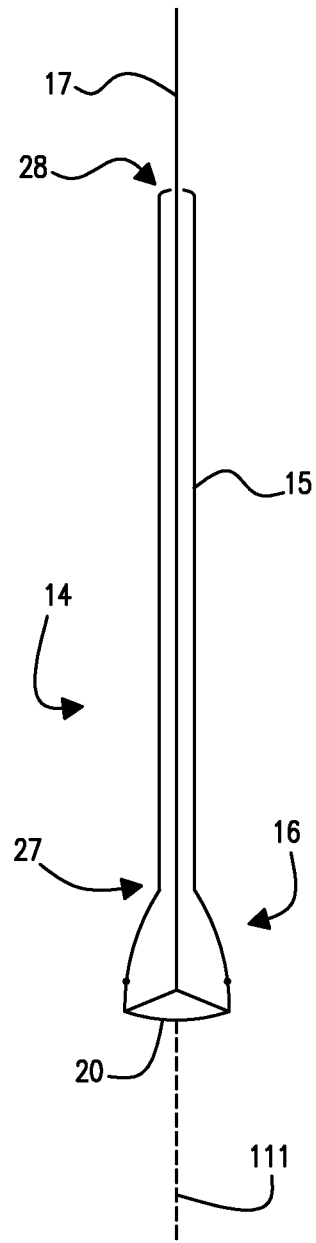
FIG. 5 is a diagrammatic depiction of the expandable/retractable biopsy sampling device according to the present invention showing the tubular portion, the lower expandable basket-like tip depicted in an expanded state, and the draw wire extending from the tip through the length of the tubular portion.

From a comparative inspection of FIG. 5 versus FIG. 4, the reader will note that the diagrammatic depictions of the expandable/retractable biopsy sampling device 14 show the tubular portion or member 15, the lower expandable basket-like tip 16, and the draw wire 17 or tip retraction means in different configurations. Perhaps most notably, the basket-like tip construction 16 is depicted in a retracted state in FIG. 4, and in an expanded state in FIG. 5.

FIGS. 6 and 7 then follow FIGS. 4 and 5 and include the outer catheter member 11, showing or depicting in FIG. 7 the expandable/retractable biopsy sampling device 14 being directed (as at 103) in a first direction and axially displaced relative to the stationary outer catheter 11, the basket-like tip construction 16 being located within the inner diameter of the outer catheter 11. The inner surfacing or inner wall 40 of the outer catheter 11 holds the tip construction 16 in a spring-biased retracted state.

In FIG. 7, the expandable/retractable biopsy sampling device 14 is being further directed (as at 103) in the first direction and axially displaced relative to the stationary outer catheter 11 such that the basket-like tip construction 16 exits or emerges from the end 18 of the outer catheter 11, and thus being free of the inner wall or inner surfacing 40 constraints of the outer catheter 11, the basket-like tip construction 16 expands into a tissue sampling configuration. The circular terminus 20 is depicted in a fully open, tissue-cutting or tissue-slicing configuration in FIG. 7.

FIGS. 8 and 9 then follow FIGS. 6 and 7 and include the outer catheter member 11 and the expandable/retractable biopsy sampling device 14 being directed (as at 104) in a second direction opposite the first direction 103 and axially displacing the tubular portion or displacement member 15 relative to the stationary catheter tubular portion 19 of the outer catheter 11. The circular terminus 20 is depicted in a cinched closed, tissue-cut/enclosed configuration as at 21 in FIG. 8.

The basket-like tip construction 16 is depicted as being drawn towards the end 18 of the outer catheter 11 and when the tip construction 16 engages said end 18, the wall or surfacing 18 forces the tip construction 16 into a collapsed state that is receivable within the inner surfacing 40 of the outer catheter 11, thereby compressing and holding secure the volumetric biopsy tissue sample as at 105.

In FIG. 9, the expandable/retractable biopsy sampling device 14 is being further directed (as at 104) in the second direction and axially displaced relative to the stationary outer catheter 11 such that the basket-like tip construction 16 enters and collapses or retracts within the inner surfacing 40 of the tubular portion 19 of the outer catheter 11, and is thus again bound by the inner diameter constraints of the outer catheter 11, the volumetric biopsy tissue sample being basket secured via the basket-like tip construction 16 in an retracted state.

Referencing FIGS. 10 and 11, the reader will note an enlarged axial end view or depiction of the expandable/draw wire-retractable distal portion as at 22. Conceivably, the expandable/draw wire-retractable distal portion 22 may be preferably and circumferentially outfitted with (spring-) biased hinge means as at 23 outfitted with or coupled to the expandable-collapsible retractable proximal portion 24 of the basket-like tip construction 16. The expandable/draw wire-retractable portion 22 conceivably comprises a number of interfolded, hinge means-mounted cutting blades 25, wherein each blade 25 preferably comprises a razor sharp cutting edge as at 26 for cutting or slicing into the targeted tissue mass 102.

The tip retraction means according to the present invention primarily operate to retract the tip construction 16 after the tip construction 16 has sliced into the tissue mass 102. The tip retraction means are preferably exemplified by a draw wire or tensile element 17. When tension is applied to the draw wire or tensile element 17, as anchored to a select blade 25, the overlapping blades 25 simultaneously collapse upon and sever the end of the volumetric tissue sample 105 for enclosing the volumetric biopsy tissue sample 105 within the volumetric spaced defined by the expandable-retractable basket-like tip construction 16.

The expandable-retractable biopsy sampling device 14 is then retracted as it is axially displaced back into the outer catheter 11 with the biopsy sample 105 enclosed within the retracted expandable tip construction 16. The expandable-retractable biopsy sampling device 14 is then removed from the outer catheter 11.

When the expandable-retractable biopsy sampling device 14 is thereby removed from the patient, the draw wire 17 is then relaxed and the biased hinge means 23 enable the expandable/draw wire-retractable portion 22 of the tip construction of the device to re-expand. The volumetric biopsy tissue sample 105 is then released and placed in a sterile container to be sent to the pathology department for pathology evaluation.

The tissue sample securement apparatus according to the present invention thus basically functions to secure a volumetric tissue sample as at 105. The tissue sample securement apparatus according to the present invention may be said to preferably comprise, in combination, an expandable-retractable tissue sampling device as at 14, and a catheter member as at 11.

The tissue sampling device 14 preferably comprises a tubular portion or axial displacement member as at 15 and an expandable tip construction as at 16. The tubular portion or axial displacement member 15 comprises a distal tube end as at 27 and a proximal tube end as at 28. The tip construction 16 is extendable from the distal tube end 27.

The catheter member 11 preferably comprises a distal catheter end 18, a proximal catheter end 29, and an inner catheter surface as at 40. The tubular portion or displacement member 15 is being (telescopically) receivable within the catheter member 11 and is axially displaceable relative thereto. The tip construction 16 is receivable within the catheter member 11 when the tubular portion 15 is axially displaced in a first direction as at 104.

The inner catheter surfacing 40 retains the tip construction 16 in a spring-actuated state when the tip construction 16 is received in the catheter member 11. The tubular portion 15 is displaceable in a second direction (as at 103) for emerging the tip construction 16 from the catheter member 11. The tip construction 16 is expandable when removed from the catheter member 11, and the expanded tip construction 16 may thus slice or cut into a volumetric tissue sample or target tissue mass 102 when displaced in the second direction.

The tissue sample securement apparatus according to the present invention further preferably comprises certain tip retraction means for retracting the tip construction 16 after the tip construction 16 has sliced into the target tissue mass 102. The tip retraction means according to the present invention primarily function to sever and securing a volumetric tissue sample 105 from the target tissue mass 102 via the tip construction 16.

The tip retraction means are manually operable, and preferably comprise a tensile member as at 17. The tensile member 17 extends through or in adjacency to the tubular portion or axial displacement member 15, and is preferably connected to the tip construction 16. The tensile member 17 being (manually) forceable in the first direction 104 for selectively retracting a member-retractable distal portion 22 of the tip construction 16.

The tissue sample securement apparatus according to the present invention may further preferably comprise a member sheath as at 41. The member sheath 41 is preferably integrally formed with the tubular member 15 and sheath-protects the tensile member 17. In other words, the draw wire or tensile element 17 is preferably sheathed by the member sheath 41 for its general protection.

The tissue sample securement apparatus according to the present invention further preferably comprises a plurality of circumferentially spaced cutting blades as at 25. The cutting blades 25 preferably overlap laterally as generally and comparatively depicted in FIGS. 10 and 11, and are mounted to the tubular portion or displacement member 15 distally via hinge means 23 for enabling pivotal motion 112 of the cutting blade(s) 25 about a plurality of hinge axes of rotation as at 110 thereby enabling expansion and retraction of the tip construction 16. The hinge axes of rotation 110 are orthogonal to the device axis as at 111.

While the foregoing sets forth much specificity, the foregoing should not be construed as setting forth limitations on the present invention, but as setting forth certain preferred embodiments and supporting certain methodology thereby. For example, it is contemplated that the present invention essentially provides a tissue sample securement apparatus for securing a volumetric tissue sample.

The tissue sample securement apparatus according to the present invention is believed to essentially comprise an expandable-retractable tissue sampling device operable in connection with an outer tubular catheter construction. The tissue sampling device (as at 14) preferably comprises a tubular portion as at 15, an expandable basket-like tip construction as at 16, and a tensile member as at 17.

The tubular portion 15 preferably comprises a distal tube end as at 27 and a proximal tube end as at 28. The basket-like tip construction 16 extends from the distal tube end 27, and the tensile member extends through the tubular portion 15 and is connected to the basket-like tip construction 16 for selectively retracting a member-retractable distal portion (as at 22) of the basket-like tip construction 16. The selectively retracted distal portion 22 essentially functions to simultaneously sever and secure a volumetric tissue sample as at 105.

As stated, the foregoing specifications are believed to further support certain methodology. More particularly, the present invention contemplates a tissue sample securement method for securing a volumetric tissue sample. The tissue sample securement method according to the present invention may be said to comprise the steps of initially locating an outer catheter member (as at 11) at a target tissue mass (as at 102).

The outer catheter 11 has a proximal catheter end (as at 29) and a distal catheter end as at 18. An expandable-retractable tissue sampling device (as at 14) is insertable into the other catheter member 11, and axially displaceable and telescopically directable in a first direction through the outer catheter member 11 to the target tissue mass 102.

An expandable-retractable tip construction of the tissue sampling device is expandable at the distal catheter end 18, and cuts into the target tissue mass 102 with the tip construction 16. A tensile member (as at 17) of the tissue sampling device 14 may be tensioned thereby severing and enclosing a volumetric tissue sample (as at 105) within the tip construction 16 in a retracted state.

The expandable-retractable tissue sampling device 14 may then be axially displaced and telescopically directed in a second direction opposite the first direction through the outer catheter member 11 to remove the volumetric tissue sample 105 from the target tissue mass 102 for further delivery to a pathology department for pathology evaluation.

Accordingly, although the invention has been described by reference to certain preferred embodiments, and certain methodological steps enabled thereby, it is not intended that the novel arrangements and method be limited thereby, but that modifications thereof are intended to be included as falling within the broad scope and spirit of the foregoing disclosures, the appended drawings, and the following claims.

I claim:

1. A tissue sample securement apparatus for securing a volumetric tissue sample, the tissue sample securement apparatus comprising:

an expandable-retractable tissue sampling device, an actuator, and a catheter member, the tissue sampling device comprising a tubular portion and an expandable tip construction, the tubular portion comprising a distal tube end and a proximal tube end, the tip construction extending from the distal tube end, the catheter member comprising a distal catheter end, a proximal catheter end, and an inner catheter surface, the tubular portion being receivable within the catheter member and being axially displaceable relative thereto, the tip construction being receivable within the catheter member when the tubular portion is axially displaced in a first direction, the inner catheter surfacing retaining the tip construction in a spring-actuated state when the tip construction is received in the catheter member, the tubular portion being displaceable in a second direction for emerging the tip construction from the catheter member, the tip construction being expandable when emerged from the catheter member, the expanded tip construction for slicing into a target tissue mass when further displaced in the second direction, the actuator connected to the tip construction, the actuator capable of causing the tip construction to sever, engulf, and secure a volumetric tissue sample from the target tissue mass when actuated in a first amount;

wherein the tip construction comprises a plurality of circumferentially spaced cutting blades;

wherein the cutting blades overlap laterally and are mounted to the tubular portion distally via hinge means for enabling pivotal motion of the cutting blades about a plurality of hinge axes of rotation thereby enabling expansion and retraction of the tip construction, the hinge axes of rotation being orthogonal to the device axis.

2. The tissue sample securement apparatus of claim 1 wherein:
said actuator is capable of causing the tip construction to retract when actuated a second amount.

3. The tissue sample securement apparatus of claim 2 wherein said actuator is manually operable.

4. The tissue sample securement apparatus of claim 3 wherein actuator comprises a tensile member, the tensile member extending through the tubular portion and being connected to the tip construction, the tensile member being forceable in the first direction for selectively retracting a member-retractable distal portion of the tip construction.

5. The tissue sample securement apparatus of claim 4 comprising a member sheath, the member sheath being integrally formed with the tubular portion, the tensile member being sheathed by the member sheath, the member sheath for protecting the tensile member.

6. A tissue sampling device for securing a volumetric tissue sample, the tissue sampling device comprising:
an axial displacement member, an actuator, and an expandable tip construction, the axial displacement member comprising a distal member end and a proximal member end, the tip construction extending from the distal member end, the axial displacement member and tip construction being axially displaceable within a catheter member, the tip construction being receivable within the catheter member when the axial displacement member is axially displaced in a first direction, the catheter member retaining the tip construction in a spring-actuated state when the tip construction is received in the catheter member, the axial displacement member being displaceable in a second direction for emerging the tip construction from the catheter member, the tip construction being expandable when emerged from the catheter member, the expanded tip construction for slicing into a target tissue mass when emerged from the catheter member, the actuator connected to the tip construction, the actuator capable of causing the tip construction to sever, engulf, and secure a volumetric tissue sample from the target tissue mass when actuated in a first amount;

wherein the tip construction comprises a plurality of circumferentially spaced cutting blades;

wherein the cutting blades overlap laterally and are mounted to the tubular portion distally via hinge means for enabling pivotal motion of the cutting blades about a plurality of hinge axes of rotation thereby enabling expansion and retraction of the tip construction, the hinge axes of rotation being orthogonal to the device axis.

7. The tissue sampling device of claim 6 wherein:
said actuator is capable of causing the tip construction to retract when actuated a second amount.

8. The tissue sampling device of claim 7 wherein said actuator is manually operable.

9. The tissue sampling device of claim 8 wherein said actuator comprises a tensile member, the tensile member extending in adjacency to the axial displacement member and being connected to the tip construction, the tensile member being forceable in the first direction for selectively retracting the tip construction.

10. The tissue sampling device of claim 9 comprising a member sheath, the member sheath being cooperably associated with the axial displacement member, the tensile member being sheathed by the member sheath.

11. A tissue sample securement apparatus for securing a volumetric tissue sample, the tissue sample securement apparatus comprising:
an expandable-retractable tissue sampling device and a catheter member, the tissue sampling device comprising a tubular portion and an expandable tip construction, the tubular portion comprising a distal tube end and a proximal tube end, the tip construction extending from the distal tube end, the catheter member comprising a distal catheter end, a proximal catheter end, and an inner catheter surface, the tubular portion being receivable within the catheter member and being axially displaceable relative thereto, the tip construction being receivable within the catheter member when the tubular portion is axially displaced in a first direction, the inner catheter surfacing retaining the tip construction in a spring-actuated state when the tip construction is received in the catheter member, the tubular portion being displaceable in a second direction for emerging the tip construction from the catheter member, the tip construction being expandable when emerged from the catheter member, the expanded tip construction for slicing into a target tissue mass when further displaced in the second direction;

wherein the tip construction comprises a plurality of circumferentially spaced cutting blades;

wherein the cutting blades overlap laterally and are mounted to the tubular portion distally via hinge means for enabling pivotal motion of the cutting blades about a plurality of hinge axes of rotation thereby enabling expansion and retraction of the tip construction, the hinge axes of rotation being orthogonal to the device axis.

12. A tissue sampling device for securing a volumetric tissue sample, the tissue sampling device comprising:
an axial displacement member and an expandable tip construction, the axial displacement member comprising a distal member end and a proximal member end, the tip construction extending from the distal member end, the axial displacement member and tip construction being axially displaceable within a catheter member, the tip construction being receivable within the catheter member when the axial displacement member is axially displaced in a first direction, the catheter member retaining the tip construction in a spring-actuated state when the tip construction is received in the catheter member, the axial displacement member being displaceable in a second direction for emerging the tip construction from the catheter member, the tip construction being expandable when emerged from the catheter member, the expanded tip construction for slicing into a target tissue mass when emerged from the catheter member;

wherein the tip construction comprises a plurality of circumferentially spaced cutting blades; and wherein the cutting blades overlap laterally and are mounted to the tubular portion distally via hinge means for enabling pivotal motion of the cutting blades about a plurality of hinge axes of rotation thereby enabling expansion and retraction of the tip construction, the hinge axes of rotation being orthogonal to the device axis.

* * * * *